United States Patent [19]

Kornher et al.

[11] Patent Number: 4,879,214

[45] Date of Patent: Nov. 7, 1989

[54] DIFFERENTIATION OF NUCLEIC ACID SEGMENTS ON THE BASIS OF NUCLEOTIDE DIFFERENCES

[75] Inventors: John S. Kornher, Claymont; Kenneth J. Livak, Wilmington, both of Del.

[73] Assignee: E. I. Du Pont de Nemours and Company, Wilmington, Del.

[21] Appl. No.: 272,068

[22] Filed: Nov. 15, 1988

[51] Int. Cl.$^4$ .............................................. C12Q 1/68
[52] U.S. Cl. ................................. 08/10/89; 435/91; 935/1; 935/2; 935/3; 935/8; 935/17; 935/18; 935/76; 935/77
[58] Field of Search ..................... 435/6, 91; 935/1, 2, 935/3, 8, 17, 18, 76, 77

[56] References Cited

U.S. PATENT DOCUMENTS 4,749,647  6/1988  Thomas et al. ........................ 435/6
4,775,619  10/1988  Urdea ....................................... 435/6
4,794,075  12/1988  Ford et al. .............................. 435/6

OTHER PUBLICATIONS

Berger et al. (ed), Methods in Enzymology 152:64(1987).
Engelke et al., Proc. Natl. Acad. Sci. USA 85:544–548 (1988).
Wong et al., Nature 330:384–386 (1987).
Botstein et al., Am. J. Hum. Genet. 32: 314–331 (1980).
White, Sci. Am. 258: 40–48 (1988).
Jeffreys, Cell 18:1–18 (1979).
Wallace et al., Nucl. Acids Res., 9:879–894.
Saiki et al., U.S. 4,683,194.
Landegren et al., Science 241:1077–1080 (1988).
Mundy, U.S. 4,656,127.
Novack et al., Proc. Natl. Acad. Sci., USA 83: 586–590 (1986).
Cotton et al., Proc. Natl. Acad. Sci. USA 85: 4397–4401 (1988).
Shenk et al., Proc. Natl. Acad. Sci. USA, 72:989–993 (1975).
Meyers et al., Science, 230: 1242–1246 (1985).
Meyers et al., Nature, 313: 495–498 (1985).
Fischer et al., Proc. Natl. Sci. USA 80: 1579–1583.
Proudfoot et al., Science, 209: 1329–1336 (1980).
Lo et al., Nucl. Acids Res. 16: 8719 (1988).
Dattagupta, European patent application No. 8602766.2 (publ. 1986).
Mullis, et al., U.S. 4,683,195.
Mullis, U.S. 4,683,202.
Stoflef, et al, Science, 239: 491–497 (1988).
Klexan et al., WO 86/02929 (pub. 1986).
Ruth, WO 84/03285 (publ. 1984).
Langer et al., Proc. Natl. Acad. Sci. USA 78: 6633–6637 (1981).
Ward et al., U.S. 4,711,955.
Hobbs et al., European patent application No. 87305844.2 (publ. 1988).
Ullrich et al., Nature 313: 756–761 (1985).
Kadowaki et al., Science 240: 787–790 (1988).

Primary Examiner—Herbert J. Lilling
Assistant Examiner—Stephanie W. Zitomer

[57] ABSTRACT

A process for distinguishing nucleic acid segments on the basis of nucleotide differences, thereby providing a rapid, convenient means for detecting mutation, is disclosed. The present process comprises synthesizing separately complementary nucleic acid strands on each of at least two target nucleic acid templates using a nucleic acid polymerase and nucleoside triphosphate substrates, wherein at least one of the natural nucleoside triphosphate substrates is replaced with a mobility-shifting analog; denaturing the synthesized strands from the templates if necessary; and comparing the mobility of the separately synthesized strands through a size-fractionation medium. A difference in mobility indicates that the target nucleic acid templates contain different numbers of total nucleotides and/or different numbers of nucleotides complementary to the mobility-shifting analogs. Thus, the process of the present invention can be used to distinguish homologous DNAs or RNAs differing by nucleotide substitutions that affect the number of mobility-shifting analog residues incorporated into synthesized strands, as well as to distinguish differences due to nucleotide insertion or deletion.

10 Claims, No Drawings

DIFFERENTIATION OF NUCLEIC ACID SEGMENTS ON THE BASIS OF NUCLEOTIDE DIFFERENCES

BACKGROUND OF THE INVENTION

1. Field of the Invention

This invention relates to a rapid, convenient process for distinguishing target nucleic acid segments on the basis of nucleotide differences wherein the nucleic acid segments may differ in size, base composition, or both.

2. Summary of the Background

The science of genetics is based on the identification and characterization of mutations, which are changes in DNA (DNA polymorphisms) due to nucleotide substitution, insertion, or deletion. Thus, many techniques have been developed to compare homologous segments of DNA to determine if the segments are identical or if they differ at one or more nucleotides. Practical applications of these techniques include genetic disease diagnoses, forensic techniques, and human genome mapping.

The most definitive method for comparing DNA segments is to determine the complete nucleotide sequence of each segment. Examples of how sequencing has been used to study mutations in human genes are included in the publications of Engelke, et al., Proc. Natl. Acad. Sci. U.S.A. 85:544–548 (1988) and Wong, et al., Nature 330:384–386 (1987). At the present time, it is not practical to use extensive sequencing to compare more than just a few DNA segments, because the effort required to determine, interpret, and compare sequence information is time-consuming.

For genetic mapping purposes, the most commonly used screen for DNA polymorphisms arising from mutation consists of digesting DNA with restriction endonucleases and analyzing the rsulting fragments by means of Southern blots, as described by Botstein, et al.,Am. J. Hum. Genet. 32:314–331 (1980); White, et al., Sci. Am. 258:40–48 (1988). Mutations that affect the recognition sequence of the endonuclease will preclude enzymatic cleavage at that site, thereby alterning the cleavage pattern of that DNA. DNAs are compared by looking for differences in restriction fragment lengths. A major problem with this method (known as restriction fragment length polymorphism mapping or RFLP mapping) is its inability to detect mutations that do not affect cleavage with a restriction endonuclease. Thus, many mutations are missed with this method. One study, by Jeffreys, Cell 18:1–18 (1979), was able to detect only 0.7% of the mutational variants estimated to be present in a 40,000 base pair region of human DNA. Another problem is that the methods used to detect restriction fragment length polymorphisms are very labor intensive, in particular, the techniques involved with Southern blot analysis.

A technique for detecting specific mutations in any segment of DNA is described in Wallace, et al., Nucl. Acids Res. 9:879–894 (1981). It involves hybridizing the DNA to be analyzed (target DNA) with a complementary, labeled oligonucleotide probe. Due to the thermal instability of DNA duplexes containing even a single base pair mismatch, differential melting temperature can be used to distinguish target DNAs that are perfectly complementary to the probe from target DNAs that differ by as little as a single nucleotide. An adaptation of this technique, described by Saiki, et al., U.S. Pat. No. 4,683,194, can be used to detect the presence or absence of a specific restriction site. In Saiki's adaptation, an end-labeled oligonucleotide probe spanning a restriction site is hybridized to the target DNA. The hybridized duplex of DNA is then appropriately incubated with the restriction enzyme for that site. Only paired duplexes between probe and target that reform the restriction site will be cleaved by digestion with the restriction endonuclease. Detection of shortened probe molecules indicates that the specific restriction site is present in the target DNA. In a related technique, described in Landegren, et al., Science 241:1077–1080 (1988), oligonucleotide probes are constructed in pairs such that their junction corresponds to the site on the DNA being analyzed for mutation. These oligonucleotides are then hybridized to the DNA being analyzed. Base pair mismatch between either oligonucleotide and the target DNA at the junction location prevents the efficient joining of the two oligonucleotide probes by DNA ligase. A major problem with these and other oligonucleotide techniques is that the mutation must already be characterized as to type and location in order to synthesize the proper probe. Thus, techniques using oligonucleotide probes can be used to assay for specific, known mutations, but they cannot be used generally to identify previously undetected mutations.

In the technique described in Mundy, U.S. Pat. No. 4,656,127, specific mutations can be detected by first hybridizing a labeled DNA probe to the target nucleic acid in order to form a hybrid in which the 3' end of the probe is positioned adjacent to the specific base being analyzed. Then, a DNA polymerase is used to add a nucleotide analog, such as a thionucleotide, to the probe strand, but only if the analog is complementary to the specific base being analyzed. Finally, the probe-target hybrid is treated with exonuclease III. If the nucleotide analog has been incorporated, the labeled probe is protected from nuclease digestion. Absence of a labeled probe indicates that the analog and the specific base being analyzed were not complementary. As with abovediscussed techniques involving oligonucleotides, this method detects specific mutations, but it cannot be used in a general manner to detect all possible nucleotide differences.

Nucleotide differences between two DNA sequences also can be studied by forming a heteroduplex between the two DNAs of interest. Base pair mismatches will occur within the heteroduplex at points where the sequences differ. A number of methods have been developed to detect such mismatches. Chemical probes for mismatches exist that specifically react with those atoms in the base normally involved in hydrogen bonding, see, e.g., Novack, et al., Proc. Natl. Acad. Sci. U.S.A. 83:586–590 (1986); Cotton, et al., Proc. Natl. Acad. Sci. U.S.A. 85:4397–4401 (1988). These chemically altered sites are susceptible to chemical cleavage, whereas a perfectly paired duplex is not. Problems with this technique include: (i) toxicity of the chemical reagents and (ii) efficiency of much less than 100% for the reactions with unpaired bases. Another approach to mismatch detection is based upon the ability of certain nucleases to recognize and cleave these sites. $S_1$ nuclease and RNase A have been shown effective in mismatch detection and cleavage, see, e.g., Shenk, et al., Proc. Natl. Acad. Sci. U.S.A. 72:989–993 (1975); Myers, et al., Science 230:1242–1246 (1985). Neither of these enzymes, however, cleaves at all possible mismatched base pairs. There is also considerable background associated with nuclease cleavage at perfectly paired sites in the duplex.

Myers, et al., Nature 313:495-498 (1985), and Fischer, et al., Proc. Natl. Acad. Sci. U.S.A. 80:1579-1583 (1983), have demonstrated that mismatched base pairs within a heteroduplex alter its melting properties with respect to a perfectly paired homoduplex. These altered melting properties can be observed electrophoretically on a gel containing an exponential gradient of denaturant. A serious drawback to this technique is the difficulty of manipulating and processing these gels. Another problem is the inability of this technique to detect uniformly all base pair mismatches along a given heteroduplex. The resolving power of these gels is reduced with increasing GC content of the heteroduplex, and thus mutations in a GC-rich domain are more difficult to detect than mutations in a domain with a lower GC content.

The primer extension process described in Proudfoot, et al., Science 209:1329-1336 (1980), has been widely used to study the structure of RNA and also has been used to characterize DNA, see, e.g. Engelke, et al., Proc. Natl. Acad. Sci. U.S.A. 85:544-548 (1988). This process consists of hybridizing a labeled oligonucleotide primer to a template RNA or DNA and then using a DNA polymerase and deoxynucleoside triphosphates to extend the primer to the 5' end of the template. The labeled primer extension product is then fractionated on the basis of size, usually by electrophoresis through a denaturing polyacrylamide gel. When used to compare homologous DNA segments, this process can detect differences due to nucleotide insertion or deletion. Because size is the sole criterion used to characterize the primer extension product, this method cannot detect differences due to nucleotide substitution.

In order to be useful for a wide variety of applications, a technique to detect nucleotide differences (mutations) in DNA should be simple, fast, and able to detect any nucleotide difference that might occur and, additionally, should not be dependent on the prior characterization of the nucleotide difference. The currently available detection techniques discussed above are deficient in one or more of these areas. Many of the problems associated with these techniques are overcome by the present invention.

The process of the present invention exploits the fact that the incorporation of some nucleotide analogs into DNA causes an incremental shift in mobility when the DNA is subjected to a size fractionation process, such as electrophoresis. Others have noted that nucleotide analogs can cause an electrophoretic mobility shift, see, e.g., Lo, et al., Nucl. Acids Res. 16:8719 (1988); Dattagupta, et al., European Patent Application No. 8602766.2 (published 1986), but it has not been realized, nor is it obvious, that this property of nucleotide analogs can be used as the basis for a process to identify previously undetected mutations.

SUMMARY OF THE INVENTION

The present invention provides a process for distinguishing nucleic acid segments on the basis of nucleotide differences, which comprises synthesizing separately complementary nucleic acid strands on each of at least two target nucleic acid templates using a nucleic acid polymerase and nucleoside triphosphate substrates, wherein at least one of the natural nucleoside triphosphate substrates is replaced with a mobility-shifting analog; denaturing the synthesized strands from the templates if necessary; and comparing the mobility of the separately synthesized strands through a size-fractionation medium.

DETAILED DESCRIPTION OF THE INVENTION

The present invention discloses a process for distinguishing nucleic acid segments on the basis of one or more nucleotide differences. This process has utility as a rapid, convenient means to identify previously undetected mutations due to nucleotide substitution, insertion, or deletion.

In sum, this process uses a nucleic acid polymerase to synthesize separately complementary nucleic acid strands on each of at least two target nucleic acid templates, the sequence and number of nucleotides in the synthesized strands being determined by the sequence and length of the target nucleic acid templates. At least one of the natural nucleoside triphosphates is replaced with a mobility-shifting analog. The separately synthesized strands prepared from different target nucleic acid templates are compared by subjecting the synthesized strands to passage through a size-fractionation medium. Synthesized strands that are the same length but differ in the number of mobilityshifting analog molecules per strand will exhibit different mobilities when fractionated according to size. The detection of a mobility difference indicates that the original target nucleic acid segments are not identical. Thus, the process of the present invention provides a rapid assay for distinguishing target nucleic acid segments wherein the nucleic acid segments may differ in size, base composition, or both.

Target nucleic acid segments to be analyzed by this process may be DNA or RNA, and the DNA or RNA may be double stranded or single stranded. As described in more detail in Mullis, et al., U.S. Pat. No. 4,683,195 and Mullis, U.S. Pat. No. 4,683,202, any source of nucleic acid, in purified or nonpurified form, can be utilized as the starting nucleic acid or acids, if it contains, or is suspected of containing, the target nucleic acid. The target nucleic acid can be only a fraction of a larger molecule or can be present initially as a discrete molecule. Additionally, the target nucleic acid may constitute the entire nucleic acid or may be a fraction of a complex mixture of nucleic acids.

In the first step of the present process, complementary nucleic acid strands are synthesized separately on at least two target nucleic acid templates using a nucleic acid polymerase and nucleoside triphosphate substrates, wherein at least one of the natural nucleoside triphosphate substrates is replaced with a mobility-shifting analog. A preferred embodiment of this process exploits the ability of most DNA polymerases and some RNA polymerases to perform primer extension reactions. Execution of a primer extension reaction requires a nucleic acid substrate consisting of a primer hybridized to a template strand such that the 3' end of the primer is recessed relative to the 5' end of the template strand. As primer extension methods are most commonly practiced, the primer is DNA, the template strand is either DNA or RNA, and a DNA polymerase is used to extend the primer. The basic elements required for execution of primer extension reactions are reviewed in Mullis, et al., U.S. Pat. No. 4,683,195, and Mullis, U.S. Pat. No. 4,683,202, and include definition of a primer, size of primers, preparation of oligonucleotide primers, methods for separating strands of double stranded nucleic acid, preferable ratio of primer to template, conditions for mixing and annealing primer to template strand, and conditions for extending the primer to produce synthesized strands.

Any target nucleic acid segment can be used as a template and analyzed by the primer extension process. It is only necessary that sufficient sequence information at one or both ends of the target nucleic acid be known so that an oligonucleotide primer or primers can be prepared that will hybridize to the template strand containing the target nucleic acid segment at a position such that the extension product synthesized from the primer will use the target nucleic acid segent as template. For single stranded target nucleic acid segments, the template strand is the strand that contains the target nucleic acid segment. For double stranded target nucleic acid segments, the template strand may be either of the two strands that contains the target nucleic acid segment, and which strand is used as a template is determined by the selection of the primer. Additionally, if double stranded, the nucleic acid containing the template strand is treated to separate the strands before being used to prepare primer extension products. The primer and template strands are mixed, allowed to anneal, and then treated with a nucleic acid polymerase.

For DNA template strands, suitable commercially available DNA polymerases include the DNA polymerase obtained from the thermophilic bacterium *Thermus aquaticus* (Taq polymerase), *E. coli* DNA polymerase I, Klenow fragment of *E. coli* DNA polymerase I, reverse transcriptase, phage T4 DNA polymerase, and phage T7 DNA polymerase. Structural variants and modified forms of these and other DNA polymerases also can be used. For RNA templates, reverse transcriptase is an example of a DNA polymerase that can be used. In the presence of the four natural deoxyribonucleoside triphosphates (dNTPs), or analogs for one or more of the dNTPs, the DNA polymerase will extend the length of the oligonucleotide primer in the 3' direction. For the method of this invention at least one of the natural dNTPs is replaced with a mobility-shifting analog. Extension is achieved by the attachment of the 5' phosphate group of an incorporating nucleotide to the 3' hydroxyl of the previously incorporated nucleotide. The sequence of the extension product will be complementary to the corresponding sequence of the template strand. The reaction terminates when every base in the template strand is represented in the primer extension product.

Adaptations and alternatives of the primer extension technique can also be used with the process of the present invention. Double stranded nucleic acid targets can be used to generate both the template and primer strands, thereby eliminating the primer-template annealing step. By enzymatic or chemical treatment of the double stranded nucleic acid, molecules can be produced that have a recessed 3' strand and an overhanging 5' strand and thus are substrates for nucleotide addition by a DNA polymerase. For example, cleavage of DNA with many restriction enzymes generates 5' overhangs that are substrates for DNA polymerases. Also, there are 3' exonucleases that remove 3' nucleotides from double-stranded DNA, producing molecules with 3' recessed strands and 5' overhanging strands.

By using an RNA-dependent RNA polymerase, such as QB replicase, primer extension reactions can be performed using an RNA template and an RNA, rather than DNA, primer. In this case, the mobility-shifting analogs would be ribonucleotides rather than the deoxyribonucleotides used in conventional primer extension.

If a DNA-dependent RNA polymerase is used, such as SP6 RNA polymerase, T3 RNA polymerase, T7 RNA polymerase, or E. coli RNA polymerase, the need for a primer is eliminated entirely. What is required is a double stranded DNA template that contains a specialized sequence element called a promoter. Each RNA polymerase has its own specific set of promoter sequences, typically 15 to 35 nucleotides in length. In Mullis, et al., U.S. Pat. No. 4,683,195, and Mullis, U.S. Pat. No. 4,683,202, a method is described for attaching a non-complementary sequence, such as an RNA polymerase promoter sequence, to any segment being amplified by the polymerase chain reaction (PCR) disclosed in these patents. A procedure for preparing RNA transcripts using PCR-amplified templates is described in Stoflet, et al., Science 239:491-497 (1988). The RNA polymerase binds to the promoter element and initiates RNA synthesis at a defined site on the DNA template, thus generating an RNA transcript with a defined 5' end. By replacing at least one of the four natural ribonucleoside triphosphates with a mobility-shifting analog, these analogs can be incorporated into the RNA transcript. The 3' end of the RNA transcript is usually determined by having a defined end to the DNA template. RNA transcripts can be analyzed by size fractionation in the same manner as primer extension products.

Mullis, et al., U.S. Pat. No. 4,683,195,and Mullis, U.S. Pat. No. 4,683,202, disclose PCR, which can can be used to amplify any specific segment of nucleic acid. PCR is basically a series of successive primer extension reactions, and it is an excellent and preferred process to use for preparing target nucleic acid templates for the process of the present invention because the final products of PCR are double stranded DNA segments with defined ends. The ends of each of the amplified DNA segments are determined by the 5' ends of the two oligonucleotide primers used to initiate and maintain the PCR process. Mobility-shifting nucleotide analogs can be incorporated into DNA as part of the PCR process by replacing at least one of the four natural deoxyribonucleoside triphosphates normally used in PCR with a mobility-shifting analog. By performing PCR in this manner, homologous DNA segments can be simultaneously amplified and prepared to detect mobility differences that would indicate nucleotide substitutions, insertions, or deletions.

In the present process, the critical feature is the synthesis of nucleic acid strands complementary to target nucleic acid segments wherein at least one of the natural nucleoside triphosphate substrates is replaced with a mobility-shifting nucleotide analog that changes the migration properties of the synthesized strand through size-fractionation media. It is known in the prior art that when nucleic acid strands synthesized with natural nucleotides are fractionated on the basis of size, the mobility of the synthesized strand through a separation medium is determined by the total number of nucleotides present in the synthesized strand. When comparing synthesized strands prepared from homologous target nucleic acids and containing only natural nucleotides, a difference in mobility indicates that the target nucleic acids contain different numbers of nucleotides. Thus, target nucleic acids with nucleotide insertions or deletions can be distinguished by techniques known in the art, however nucleotide substitutions cannot be detected by such techniques.

The present invention discloses the substitution of mobility-shifting analogs for natural nucleotides. A mobility-shifting nucleotide analog is any nucleotide analog (i) that can be incorporated specifically into a growing nucleic acid strand in place of one of the natural nucleotides, (ii) that after being incorporated can function as substrate for further additions of nucleotides to the growing nucleic acid strand without terminating synthesis of the growing strand, and (iii) that causes the nucleic acid to migrate at a position different than that expected from its length when analyzed by passage through a size-fractionation medium. For example, incorporation of biotin-11-dUTP (Enzo Diagnostics, Inc., New York, N.Y.), an analog of TTP, into a DNA strand causes a one nucleotide mobility shift when the DNA is fractionated on a sequencing gel. This means that, for each biotin-11-dUTP residue incorporated, the DNA strand migrates at a position one nucleotide slower than is expected based on the length of the DNA strand.

Examples of commercially available compounds that can be used as mobility-shifting analogs include biotin-11-dUTP, biotin-11-dCTP, and biotin-11-UTP (Enzo Diagnostics, Inc., New York, N.Y.); biotin-7-dATP (Bethesda Research Laboratories, Gaithersburg, Md.); digoxigenin-11-dUTP (Boeringer Mannheim Biochemicals, Indianapolis, Ind.); and 5-([N-biotinyl]-3-aminoallyl)-2'-deoxyuridine 5'-triphosphate (Bio-4-dUTP), 8-(N-[N-biotinyl-ε-aminocaproyl]-8-aminohexylamino)adenosine 5'-triphosphate (Bio-14-ATP), and N6-(N-[N-biotinyl-ε-aminocaproyl]-6-aminohexyl-carbamoylmethyl)adenosine 5'-triphosphate (Bio-17-ATP) (Sigma Chemical Co., St. Louis, Mo.). These compounds are commercially available because they contain biotin or digoxigenin, which are small molecules that can be detected by convenient and sensitive assay. For the purposes of this invention, it is not required that the mobility-shifting nucleotide analog also contain a moiety that is used for detection such as biotin, digoxigenin, or some other reporter. The commercially available compounds listed above are a small subset of the following families of modified nucleoside triphosphates that can be used as mobility-shifting analogs.

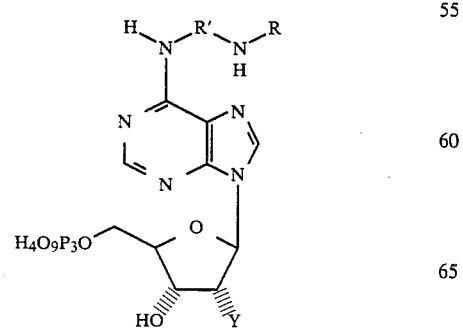

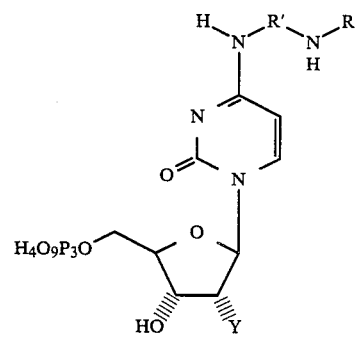

described by Klevan, et al., WO 86/02929 (published 1986);

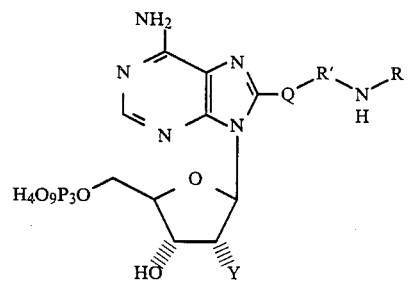

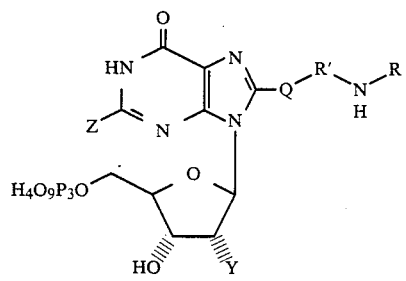

described by Ruth, WO 84/03285 (published 1984); and

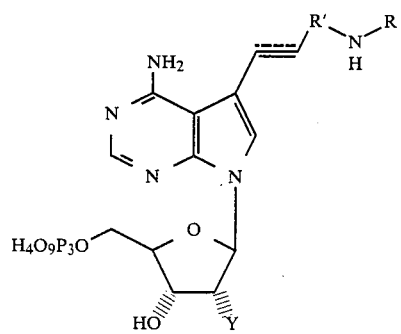

-continued

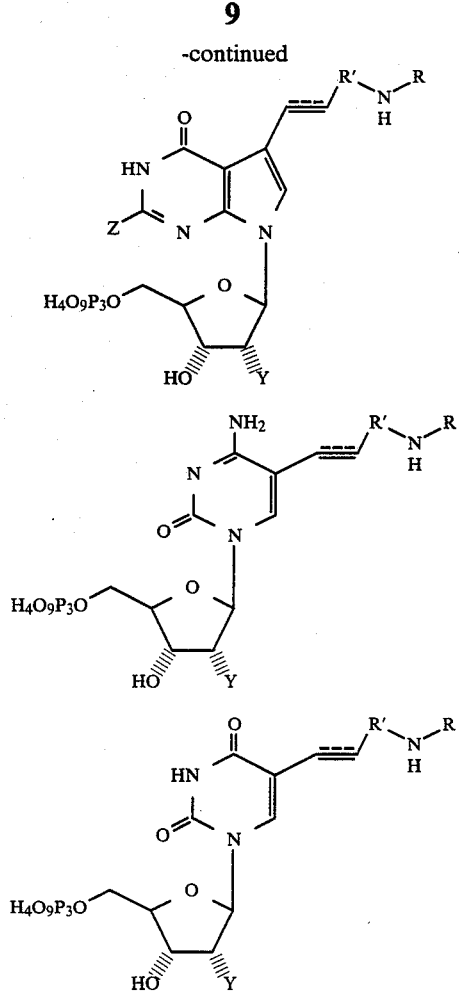

described by Langer, et al., Proc. Natl. Acad. Sci. U.S.A. 78:6633-6637 (1981); Ward, et al., U.S. 4,711,955; Hobbs, et al., European Patent Application No. 87305844.0 (published 1988). In the above structures, ≡≡≡ = double or triple bond
Q=O, S, or NH
Y=H or OH
Z=H or NH$_2$
R=H, acyl, aryl, heterocyclic, or alkyl radical, wherein the alkyl radical can be straight-chained, branched, or cyclic. R can optionally contain double bonds, triple bonds, aryl groups, or heteroatoms, such as N, O, S, or halogens. The heteroatoms can be part of such functional groups as ethers, thioethers, esters, amines, amides, or heterocycles.

R′=substituted or unsubstituted diradical moiety of 1-20 atoms. R′ can be straight-chained C$_1$-C$_{20}$ alkylene and optionally can contain double bonds, triple bonds, aryl groups, or heteroatoms, such as N, O, or S. The heteroatoms can be part of such functional groups as ethers, thioethers, esters, amines, or amides. Substituents on R′ can include C$_1$-C$_6$ alkyl, aryl, ester, ether, amine, amide, or chloro groups.

For generality, the above nucleotide analogs are shown with the triphosphate group in the tetraacid form. When dissolved in water, the tetraacid form of these compounds slowly decomposes due to the acidity of the resulting solution (pH approximately 2). These compounds are therefore generally prepared and used as tri- or tetrabasic salts at about pH 4 to 10.

A single mobility-shifting analog cannot be used to detect all possible nucleotide substitutions. One way to detect all possible substitutions is to have separate mobility-shifting analogs for each of the four natural nucleotides. Then, by performing four separate strand synthesis reactions, one with each of the analogs, target nucleic acids can be assayed for differences involving any one of the four natural nucleotides. For double stranded nucleic acid targets, all possible nucleotide substitutions can be analyzed with just two mobility-shifting analogs by using each of the two strands as template strand in separate strand synthesis reactions. For synthesized DNA strands, one analog must be a dATP or TTP analog, and the other analog must be a dCTP or dGTP analog. For synthesized RNA strands, one analog must be an ATP or UTP analog, and the other analog must be a CTP or GTP analog. Also, for primer extension reactions, a separate primer complementary to each of the template strands is required. This analysis of double stranded targets with just two analogs is possible because of the complementary nature of double stranded nucleic acids. Any change that affects an A in one strand must necessarily affect a T in the opposite strand, and any change that affects a G in one strand must necessarily affect a C in the opposite strand. Thus, by using two sets of two separate strand synthesis reactions to test both strands of the target nucleic acid with, for example, a T and a C analog, all possible single nucleotide substitutions can be detected.

After the complementary nucleic acid strands are separately synthesized on at least two target nucleic acid templates, wherein at least one of the natural nucleotides is replaced with a mobilityshifting analog, the next step of the present process is to denature the synthesized strands from their respective templates, if the method of preparation results in synthesized strands remaining hybridized to template strands. The duplex must be denatured so that the synthesized strands can be analyzed by size fractionation. Mullis, et al., U.S. Pat. No. 4,683,195, and Mullis, U.S. Pat. No. 4,683,202, describe a variety of treatments that can be used to denature or separate the strands of double stranded nucleic acid.

Next, the mobility of the synthesized strands is compared through a size-fractionation medium. The synthesized strands prepared from target nucleic acid templates are presumed identical but may, in fact, differ by one or more nucleotide variations. When a mobility-shifting analog is used in place of one of the natural nucleotides, synthesized strands that contain different numbers of analog residues can be distinguished on the basis of differential mobility. If the synthesized strands from the different target nucleic acid templates are identical, they will all contain the same number of mobility-shifting analogs and, therefore, will migrate identically. Synthesized strands that differ in the number of mobility-shifting analog molecules per strand (because some of the target nucleic acids had a different sequence of bases) will exhibit different mobilities when fractionated according to size. Thus, use of a mobility-shifting analog makes base composition a major factor affecting mobility through a size-fractionation medium.

If the resolution of the size fractionation process is sufficient, then differences of a single nucleotide can be detected. The preferred process for size fractionation is electrophoresis through a polyacrylamide gel matrix containing a denaturant. One such denaturant is urea, although others such as formamide or sodium hydroxide may be used. This type of gel electrophoresis is used routinely in methods to determine the nucleotide sequence of DNA, and it is preferably used in the present process because it can separate nucleic acid fragments smaller than about 500 nucleotides with single nucleotide resolution. Thus, if the incremental mobility shift produced by a single analog residue is equivalent to the shift produced by an additional natural nucleotide, then nucleotide substitutions as small as a single nucleotide can be detected on such a sequencing gel.

Interpretation of mobility results requires that the synthesized strands prepared from each target nucleic acid be of discrete size. The 5' end of a primer extension product is defined by the 5' end of the primer strand used to initiate synthesis. The 3' end of a primer extension product is usually determined by having a defined 5' end on the template strand. The defined 5' end of the template strand can be a natural defined end as in mRNA; an end produced by sequence-specific enzymatic or chemical cleavage, such as the type of end produced by cleavage with a restriction endonuclease; or an end determined by the method used to produce the template strand, as is the case when the polymerase chain reaction is used to prepare target DNA. Alternatively, the 3' end of the primer extension produce can be determined by cleaving the primer extension product with a sequence-specific enzymatic or chemical cleaving agent.

In order to compare the mobility of the synthesized strands, the strands must be detected. Any method used to detect nucleic acid can be used to detect the synthesized strands containing mobility-shifting nucleotide analogs. One method is to perform the primer extension reaction with a labeled primer. Typically, oligonucleotide primers are labeled by attaching a reporter to the 5' end of the oligonucleotide. This reporter can be a radioactive isotope; a group that takes part in an enzyme or fluorescent or chemiluminescent reaction; or some other small molecule, such as biotin, that can be detected by a convenient method. Alternatively, labeling can be performed by incorporating reporter-tagged nucleotides into the synthesized strands as they are synthesized. The reporter can be attached either to a mobility-shifting nucleotide analog or to one of the other nucleotides used as substrates in the preparation of synthesized strands. The same type of reporters used to label primers can be used to label the nucleotide substrates. Another method of detection entails hybridizing a reporter-labeled probe to the synthesized strands after the size fractionation step, as in the Southern blot procedure.

The detection of newly synthesized nucleic acid strands with mobility differences indicates that the original target nucleic acid segments are not identical. When comparing synthesized strands prepared from presumed identical target nucleic acid templates, a difference in mobility indicates that the target nucleic acid templates contain different numbers of total nucleotides and/or different numbers of nucleotides complementary to the mobility-shifting analogs. Thus, as illustrated in the following Examples, the process of the present invention can be used to distinguish homologous DNAs or RNAs differing by nucleotide substitutions that affect the number of mobility-shifting analog residues incorporated into synthesized strands, as well as to distinguish differences due to nucleotide insertion or deletion.

EXAMPLES

The following examples illustrate, but do not limit, the process of the present invention. Example 1 discloses the preparation of a preferred mobility-shifting analog, 5-(Bio-AC-AP3)dCTP for the present process. Examples 2 and 3 demonstrate detection of a single nucleotide substitution that distinguishes two alleles of the human insulin receptor gene through the use of the present pocess. In Example 2, a commercially available nucleotide analog is used as the mobility-shifting analog. In Example 3, the preferred mobility-shifting analog prepared in Example 1 is used.

EXAMPLE 1

Preparation of 5-(3-(6-Biotinamido(Hexanoylamido))-1-Propynyl)-2'-Deoxycytidine 5'-Triphosphate. 5-(Bio-AC-AP3)dCTP The triethylammonium salt of 5-(3-amino-1-propynyl)-2'-deoxycytidine 5'-triphosphate, 5-(AP3)dCTP,

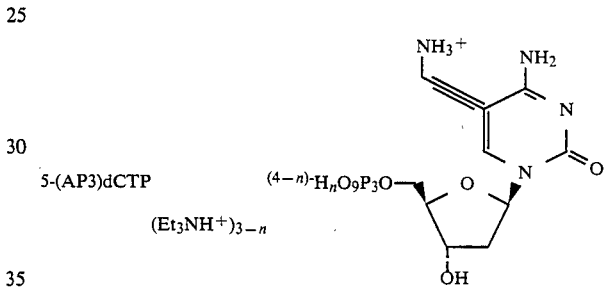

is prepared as follows.

5-(3-Trifluoroacetamido-1-propynyl)-2'-deoxycytidine [100.9 mg; 248 umol (corrected for isopropanol content)] prepared as described in Example 8 of Hobbs, et al., European Patent Application No. 87305844.0 (published 1988), was dissolved in trimethyl phosphate (0.5 mL). Phosphorus oxychloride (47 μL; 500 μmol) was added and the mixture was stirred at ambient temperature under an argon atmosphere for 30 min. The reaction mixture was added dropwise to a 1.0 M solution of tris(tri-n-butylammonium) pyrophosphate in DMF (1.5 mL; 1.5 mmol) and the resulting solution was stirred at ambient temperature under argon for 10 min. The reaction mixture was quenched by adding it dropwise to an ice-cooled solution of triethylamine (350 μL) in water (5 mL).

After standing overnight at 0° C., the solution was stripped down, redissolved in water (25 mL), and loaded onto a DEAE Sephadex A-25-120 column (1.6×55 cm) that had been equilibrated with 0.1 M aqueous triethylammonium bicarbonate (TEAB), pH 7.6. The column was eluted with a linear gradient of TEAB, pH 7.6, from 0.1 M (300 mL) to 1.0 M (300 mL), running at c. 100 mL/hr, and collecting fractions every 6 min. The eluent was monitored by absorbance at 270 nm, and the fractions corresponding to the major band (#45–50) were ooled, stripped, and co-evaporated (2x) with ethanol.

The residue was taken up in water (0.70 mL), concentrated aqueous ammonia (0.70 mL) was added, and the solution was stirred in a stoppered flask at ambient temperature for 1 hour. The solution was bubbled with argon, lyophilized, taken up in 0.1 M TEAB, and loaded onto a DEAE Sephadex column (1×30 cm). The column was eluted with a linear gradient of TEAB, pH 7.6, from 0.1 M (150 mL) to 1.0 M (150 mL), running at c. 100 mL/hr, and collecting fractions every 3 min. Again, the eluent was monitored at 270 nm and the fractions corresponding to the major peak (#28-35) were pooled, stripped, and coevaporated (2x) with ethanol. The product was assayed by UV absorbance assuming an absorption coefficient at 294 nm equal to that of the starting material in water (10,100). The yield was thus 54 μmol (21%). The product was shown to be 97.5% pure by HPLC on Zorbax SAX eluting with aqueous potassium phosphate, pH 6.5.

Next, the triethylammonium salt of 5-(3-biotinamido(hexanoylamido))-1-propynyl)-2'-deoxycytidine 5'-triphosphate, 5-(Bio-AC-AP3)dCTP,

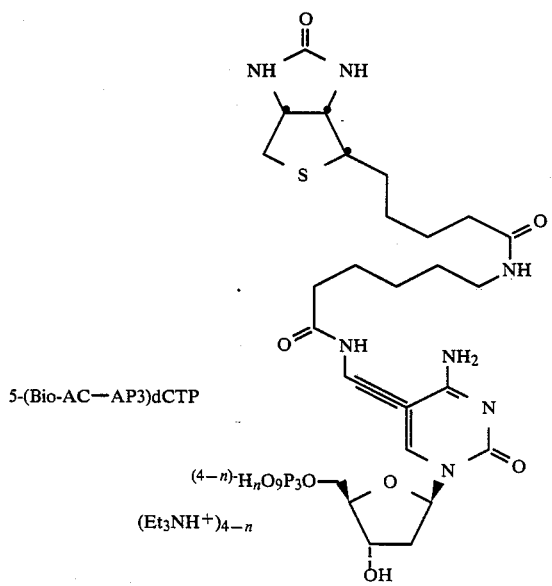

5-(Bio-AC—AP3)dCTP was prepared from 5-(3-amino-1-propynyl)-2'-deoxycytidine 5'-triphosphate, 5-(AP3)dCTP. 5-(3-Amino-1-propynyl)-2'-deoxycytidine 5'-triphosphate (30 umol) was dissolved in 1 M aqueous TEAB, pH 7.6, (600 μL) and sulfosuccinimidyl 6-(biotinamido)-hexanoate Na salt (Piece Chemical Co., Rockford, IL; 33 mg; 60 μmol) was added. The solution was held at 50° C. for 90 min and then diluted to 6 mL with water. The solution was loaded onto a DEAE Sephadex A-25-120 column (1×19 cm) that had been equilibrated with 1.0 M aqueous TEAB, pH 7.6. The column was eluted with a linear gradient of TEAB, pH 7.6, from 0.1 M (150 mL) to 1.0 M (150 mL), running at c. 100 mL/hr, collecting fractions every 3 min. The eluent was monitored by absorbance at 270 nm, and the fractions corresponding to the second peak (#22-33) were pooled, stripped, and coevaporated (2x) with ethanol. The residue was subjected to reverse phase chromatography (Baker 7025-00) on a column (1×8 cm) poured in acetonitrile/1 M aqueous TEAB, pH 7.6. The column was eluted with a step gradient of acetonitrile/1 M TEAB, pH 7.6, (0–30% acetonitrile, 2%/step, 2 mL/step, 1 fraction/step). The fractions were assayed by HPLC on a reverse phase column under conditions analogous to those used in the above separation. Starting material eluted first (#2-6) followed by the product (#7-11). The product fractions were pooled, stripped, and coevaporated (2x) with ethanol. The yield, assuming an absorption coefficient of 10,100 at 295.5 nm, was 10.5 umol (35%). HPLC on Zorbax SAX and on reverse phase showed the material to be >99% pure. The $^1$H- and $^{31}$P-NMR spectra are fully consistent with the title structure.

EXAMPLE 2

Comparison of a Segment of Two Alleles of the Human Insulin Receptor Gene that Differ by a Single Nucleotide Substitution (Primer Extension Analysis Using the Mobility-Shifting Analog, Biotin-11-dUTP)

The sequence of a 140-bp region of the structural gene encoding the human insulin receptor gene is shown below.

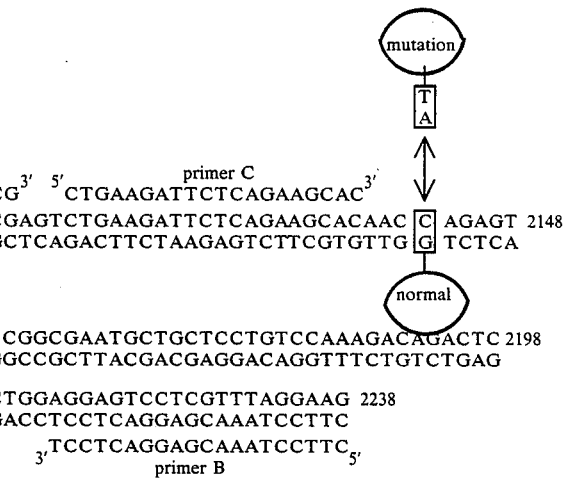

This sequence was determined from the cDNA sequence reported in Ullrich, et al., Nature 313:756 (1985). By analyzing patient DNA, Kadowaki, et al., Science 240:787-790 (1988) characterized a nonsense mutation resulting from a C to T base change at nucleotide 2143. A "normal" individual herein is heterozygous for a C at position 2143. The other individual is heteroxygous at this locus. In the heteroxygote, the paternal copy of this gene has the C to T nonsense mutation at position 2143, whereas the maternal copy has the normal C at this position. (The genomic DNA samples were obtained from Dr. Domenico Accili, National Institutes of Health, Bethesda, Md.)

PCR reactions to amplify this region from the genomic DNAs of the two individuals were performed in 0.5-mL Eppendorf microfuge tubes as follows. One microgram of genomic DNA in 5 μL Te buffer (10 mM Tris-HCl, pH 8.0; 1 mM EDTA) was placed in a microfuge tube. Separate tubes contained DNAs from individuals of different genotypes. To each tube was added 40 ng of primer A (5'-CCTGGTCTCCACCATTCG-3') in 10 μL and 40 ng of primer B (5'-CTTCCTAAAC-GAGGACTCCT-3') in 10 μL, bringing the volume to 25 μL. Four microliters of 10X Taq polymerase reaction buffer (166 mM $(NH_4)_2SO_4$; 670 mM Tris-HCl, pH 8.8; 45 mM $MgCl_2$; 100 mM 2-mercaptoethanol; 1700 ug/mL bovine serum albumin) and five units (1 μL) Taq polymerase (Perkin-Elmer Cetus, Norwalk, Conn.) were added to the reaction mix. Six microliters of stock dNTPs were added to a final concentration of 187 μM each for dATP, dGTP, dCTP, and TTP. Filter-sterilized, deionized water was added to bring the reaction volume to 40 μL. The reaction was then overlayed with mineral oil. Reactions were performed in a DNA Thermal Cycler (Perkin-Elmer Cetus, Norwalk, Conn.) as follows: 94° C. (7 min), 50° C. (3 min), 72° C. (4 min) for one cycle and then 30 cycles of 94° C. (2 min), 50° C. (3 min), 72° C. (4 min) with one second transition steps.

The PCR-amplified template was then applied to parafilm, which absorbs the mineral oil, leaving the aqueous reaction phase. Unincorporated dNTPs were removed from this aqueous phase by passing it over a G-50 spin column (New England Nuclear, Boston, Mass.). The effluent was collected in a 1.5-mL Eppendorf microfuge tube, precipitated by the addition of 1 volume of 5 M ammonium acetate and 3 volumes of absolute ethanol, and incubated in a methanol:dry ice slurry for 20 minutes. DNA was collected by centrifugation at 12,200 rpm (12,400×g) for 20 minutes at room temperature. The supernatant was pipetted off and the pellet was washed with 200 μL 70% (v/v) ethanol, and dried under vacuum for 15 min in a Speed-Vac concentrator (Savant Instruments, Inc., Hicksville, N.Y.). Each DNA sample was resuspended in 20 μL of filter-sterilized, deionized water and stored at 4° C.

Primer C (5'-CTGAAGATTCTCAGAAGCAC-3'), shown above, was selected to prime the extension reaction. Using the PCR-amplified DNA as template, this primer should yield an extension product 119 nucleotides long that includes the C to T nonsense mutation. The primer extension product from the normal allele found in the homozygote and the heteroxygote should contain 20 Ts or T analogs. The mutant allele from the heterozygote should generate a primer extension product containing 21 Ts or T analogs.

Primer C was radiolabeled with $\gamma$-$^{32}$P-ATP as follows. Twenty microliters (200 μCi) of $\gamma$-$^{32}$P-ATP (6000 Ci/mmol; New England Nuclear, Boston, Mass.) was placed in a 1.50-mL Eppendorf microfuge tube and dried under vacuum. One microliter of 10X kinase buffer (700 mM Tris-HCl, pH 7.5; 100 mM $MgCl_2$; 50 mM dithiothreitol) was combined with 8 μL (320 ng) of primer C in the presence of 5 units (1 μL) of T4 polynucleotide kinase (New England BioLabs, Beverly, Mass.) and added to the microfuge tube containing the radiolabel. The reaction was conducted at 37° C. for one hour. The reaction was stopped with 200 μL 100 mM TrisHCl, pH 7.8/1 mM EDTA and subjected to NEN-SORB® 20 chromatography (New England Nuclear, Boston, Mass.) to remove unreacted $\gamma$-$^{32}$P-ATP from the reaction. This chromatographic step involves activating the column with methanol, washing the activated column with 100 mM Tris-HCl, pH 7.8/1 mM EDTA, applying the kinased sample, washing the column with buffer and filter-sterilized, deionized water, and eluting the kinased primer from the column with 20% (v/v) ethanol. The liquid portion of the eluate was removed by vacuum in a Speed-Vac concentrator; the resulting residue was resuspended in 100 μL of filter-sterilized, deionized water, and stored at −20° C.

For the DNA from each individual of different genotype, 10 μL of PCR-amplified template was combined with 20 μL of phosphorylated primer (64 ng; 9 pmol; ~$10^7$ cpm). This mixture was heated to 94° C. for approximately 5 minutes, iced, and centrifuged at 12,200 rpm (12,400×g) for 60 seconds to sediment any condensate to the bottom of the centrifuge tube. The template:-primer mixture was stored on ice until all other reactants were combined. To a 0.5-mL Eppendorf microfuge tube the following reactants were added: 1 μL of 10X Taq polymerase reaction buffer (see above), 5 units (1 μL) Taq polymerase, and 5 μl of a dNTP stock solution that is 20 μM for each of dATP, dGTP, dCTP and biotin-11-dUTP (Enzo Diagnostics, Inc., New York, N.Y.). The control reaction was identical except for the substitution of 20 μM dUTP for the biotin analog in the dNTP stock solution. Three microliters of the template:primer mixture was immediately added to each primer extension reaction and incubated at 72° C. for 5 minutes. The reaction was iced; the liquid was removed by vacuum in a Speed-Vac concentrator for 15 to 30 minutes; and the resulting residue was resuspended in 3 μL 95% (v/v) formamide (Fluka Chemie AG, Buchs, GDR), 12.5 mM EDTA, 0.3% bromophenol blue, 0.3% xylene cyanol. The samples were placed in a boiling water bath for 5 minutes, iced, then loaded on a 6% polyacrylamide, 8 M urea (Bio-Rad, Richmond, Calif.) sequencing gel in MTB buffer (130 mM Tris, 45 mM boric acid, 2.5 mM EDTA) that had been pre-electrophoresed in MTB buffer for 30 minutes at 65 W. Samples were electrophoresed in MTB buffer at 65 W for three hours or until the xylene cyanol tracking dye was within 2 cm of the gel's bottom edge. Upon completion of electrophoresis, the gel was dried under vacuum and placed against a sheet of X-OMAT RP X-ray film (Eastman Kodak Company, Rochester, N.Y.) for autoradiographic exposure. The film was developed after 15 hour exposure at room temperature.

The conclusions of this experiment are based upon the autoradiographic evidence below.

| Control | | Biotin-11-dUTP | | 5-(Bio-AC-AP3)dCTP | |
|---|---|---|---|---|---|
| 1 | 2 | 3 | 4 | 5 | 6 |
| het | homo | het | homo | het | homo |

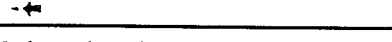

Lanes 1 and 2 show the primer extension products synthesized using dUTP in the extension reactions for, respectively, the heterozygote (het) and homozygote (homo) samples. Lane 3 (heterozygote target DNA) and lane 4 (homozygote target DNA) show the primer extension products synthesized when biotin-11-dUTP was substituted for dUTP. Lanes 1 and 2 demonstrate that substitution of dUTP for TTP in the primer extension reaction does not distinguish extension products derived from the different DNA templates. Lanes 3 and 4, as compared to lanes 1 and 2, demonstrate the electrophoretic mobility shifts that are obtained by substituting biotin-11-dUTP for dUTP in the extension reaction.

The most important result, however, is based upon a comparison of the major autoradiographic bands indicated by the arrows in lanes 3 and 4. Incorporation of biotin-11-dUTP in the primer extension reaction allows for the discrimination of two templates from the same individual that differ by a single T substitution, as evidenced by the presence of a doublet in lane 3. The doublet is observed because the primer extension product from the mutant ellele contains one more biotin-11-deoxyuridine residue than the product from the normal allele. The single band from the homozygote in lane 4 co-migrates with the lower band the doublet in lane 3, supporting the claim that the upper, more slowly migrating band in the doublet corresponds to the paternally derived mutant allele in the heterozygote.

EXAMPLE 3

Comparison of a Segment of Two Alleles of the Human Insulin Receptor Gene that Differ by a Single Nucleotide Substitution (Primer Extension Analysis Using the Mobility-Shifting Analog. 5-(Bio-AC-AP3)dCTP, from Example 1)

The PCR-amplified templates prepared in Example 2 were also used in this experiment. The radiolabeled primer C prepared in Example 2 was used to prime the extension products. As in Example 2, the primer extension products will be 119 nucleotides long and include the C to T nonsense mutation indicated in the sequence above. The primer extension product from the normal allele found in the homozygote and the heterozygote should contain 22 Cs or C analogs. The mutant allele from the heterozygote should generate a primer extension product containing 21 Cs or C analogs.

The primer extension reactions were formed exaclty as in Example 2, except the dNTP stock solution was changed to the following solution: 20 $\mu$M dATP, 20 $\mu$M dGTP, 20 $\mu$M dUTP, and 20 $\mu$M 5-(Bio-AC-AP3)dCTP (from Example 1). Primer extension products prepared in this example were co-electrophoresed with the primer extension products from Example 2 and are displayed on the autoradiogram above.

The conclusions of this experiment are based upon the autoradiographic evidence provided above. Lanes 1 and 2 show the primer extension products synthesized using dCTP for, respectively, the heterozygote and homozygote samples. Lane 5 (heterozygote target DNA) and lane 6 (homozygote target DNA) show the primer extension products synthesized using 5-(Bio-AC-AP3)dCTP. Lanes 1 and 2 demonstrate that utilizing dCTP in the primer extension reaction does not resolve extension products derived from the different DNA templates. Lanes 5 and 6, as compared to lanes 1 and 2, demonstrate the electrophoretic mobility shifts that are obtained by substituting 5-(Bio-AC-AP3)dCTP for dCTP in the extension reaction.

The most important result, however, is based upon a comparison of the major autoradiographic bands indicated by the arows in lanes 5 and 6. Incorporation of 5-(Bio-AC-AP3)dCTP in the primer extension reaction allows for the discrimination of two templates from the same individual that differ by a single C substitution, as evidenced by the presence of a doublet in lane 5. The doublet is observed because the primer extension product from the mutant allele contains one less 5-(Bio-AC-AP3)-deoxycytidine residue than the product from the normal allele. The single band from the homozygote in lane 6 co-migrates with the upper band of the doublet in lane 5, supporting the claim that the lower, more rapidly migrating band in the doublet corresponds to the paternally derived mutant allele in the heterozygote.

What is claimed is:

1. A process for distinguishing nucleic acid segments on the basis of nucleotide differences, which comprises synthesizing separately complementary nucleic acid strands on each of at least two target nucleic acid templates using a nucleic acid polymerase and nucleoside triphosphate substrates, wherein at least one of the natural nucleoside triphosphate substrates is completely replaced with a mobility-shifting analog;

and comparing the mobility of the separately synthesized strands in single-stranded form through a size-fractionation medium.

2. A process according to claim 1, wherein the nucleic acid polymerase is DNA polymerase and the nucleoside triphosphate substrates are deoxyribonucleoside triphosphate substrates.

3. A process according to claim 2 wherein the DNA polymerase is selected from the group consisting of Taq polymerase, *E. coli* DNA polymerase I, Klenow fragment of *E. coli* DNA polymerase I, reverse transcriptase, phage T4 DNA polymerase, and phage T7 DNA polymerase.

4. A process according to claim 1 wherein the nucleic acid polymerase is RNA polymerase and the nucleoside triphosphate substrates are ribonucleoside triphosphate substrates.

5. A process according to claims 1, 2, or 4 wherein the synthesis of complementary nucleic acid strands is performed by a primer extension reaction.

6. A process according to claim 5 wherein the primer extension reaction is a polymerase chain reaction (PCR).

7. A process according to claims 1, 2, or 4 wherein the mobility-shifting analog is 5-(Bio-AC-AP3)dCTP.

8. A process according to claims 1, 2, or 4 wherein the comparison of mobility of the separately synthesized strands is performed by elecrophoresis through a polyacrylamide gel matrix.

9. A process according to claim 8 wherein the polyacrylamide gel matrix contains a denaturant.

10. A process according to claim 1 wherein the synthesized strands are denatured from the templates.

* * * * *